United States Patent [19]

Seim et al.

[11] Patent Number: 5,537,213

[45] Date of Patent: Jul. 16, 1996

[54] LIGHT MEASUREMENT APPARATUS WITH RESILIENTLY BIASED SHEATH FOR DEFINING LIGHT-TIGHT ENCLOSURE AND RELATED METHOD

[75] Inventors: Torstein Seim, Sandvika; Stig M. Borch, Jar, both of Norway

[73] Assignee: Nycomed Pharma AS, Norway

[21] Appl. No.: 356,375

[22] PCT Filed: Jun. 29, 1993

[86] PCT No.: PCT/GB93/01357

§ 371 Date: Dec. 23, 1994

§ 102(e) Date: Dec. 23, 1994

[87] PCT Pub. No.: WO94/00749

PCT Pub. Date: Jan. 6, 1994

[30] Foreign Application Priority Data

Jun. 29, 1992 [GB] United Kingdom ............. 9213733

[51] Int. Cl.⁶ ..................... G01N 21/25; G01N 21/55
[52] U.S. Cl. ..................... 356/406; 356/419; 356/420; 356/445
[58] Field of Search ............. 356/416, 418–420, 356/445, 406; 359/894–895, 503, 506, 511

[56] References Cited

U.S. PATENT DOCUMENTS

| | | | |
|---|---|---|---|
| 3,263,553 | 8/1966 | Baruch | 356/414 |
| 3,718,399 | 2/1973 | Kalman | 356/210 |
| 3,807,873 | 4/1974 | Nakamori | 356/418 |
| 3,947,088 | 3/1976 | French | 350/96 |
| 4,283,146 | 8/1981 | Roussel | 356/445 |
| 4,587,422 | 5/1986 | Bowers | 250/253 |
| 4,632,559 | 12/1986 | Brunsting | 356/416 |
| 4,678,338 | 7/1987 | Kitta et al. | 356/420 |
| 4,770,536 | 9/1988 | Golberstein | 356/371 |
| 5,044,756 | 9/1991 | Gaultney et al. | 356/446 |
| 5,150,174 | 9/1992 | Ryczek et al. | 356/402 |
| 5,151,755 | 9/1992 | Seto | 356/418 |

FOREIGN PATENT DOCUMENTS 348802  3/1979  Austria .

OTHER PUBLICATIONS

International Search Report for PCT/GB93/01357 (3pages).

Primary Examiner—Frank Gonzalez
Assistant Examiner—Jason D. Eisenberg
Attorney, Agent, or Firm—Testa, Hurwitz & Thibeault

[57] ABSTRACT

Light measurement apparatus includes an elongate member which has at one end thereof light emitter(s) and light detector(s). At least the end of the elongate member that has the light emitter(s) and light detector(s) is surrounded by a resiliently biased sheath. In use, when the elongate member is applied to a surface to take a reading, the sheath defines a light-tight enclosure. A related method for determining intensity and/or color of a colored spot on a surface of a test site uses the light measurement apparatus. The method includes bringing the end of the elongate member into contact with the surface, pressing the resiliently biased sheath towards the surface to define a light-tight enclosure, and measuring the intensity and/or color of the colored spot on the surface.

14 Claims, 2 Drawing Sheets

LIGHT MEASUREMENT APPARATUS WITH RESILIENTLY BIASED SHEATH FOR DEFINING LIGHT-TIGHT ENCLOSURE AND RELATED METHOD

FIELD OF THE INVENTION

This invention relates to light measurement apparatus, in particular, though not exclusively, to colour and/or intensity measurement apparatus for use with for example a biomedical diagnostic test card.

BACKGROUND OF THE INVENTION

In recent years there have been developed test cards, e.g. solid phase immunoassay test cards, for biomedical diagnostic purposes. Such test cards are normally provided with one or more test sites, normally only a few millimeters (eg. about 5 millimeters) wide, to which a liquid sample (e.g. blood or serum) is applied. The test sites are designed to change colour in response to the presence and concentration of a particular component (e.g. a certain protein) in the liquid sample.

This colour change can, at least to a certain extent, be detected and measured by eye, by for example comparing a treated test site with a reference colour chart. Such visual techniques are, however, clearly unsatisfactory when it is desired to produce an accurate reliable measurement. To obtain reliably highly accurate measurements, an instrumental system is sought.

Measurement of colour, colour spectra and colour intensity of an opaque surface is performed by analyzing the light reflected from the surface when exposed to a defined light. It is essential that the surface area to be measured and the detection system are not exposed to external light during measurements, and light shielding of the mechanism is therefore provided. This is particularly critical if weak light sources such as light emitting diodes (LEDs) are used rather than strong sources such as xenon arc lamps or the like. It is also important that the light emitter and the light detector have defined positions relative to the surface to be measured.

Conventional instruments for analyzing surface colours tend to be large and heavy, thus not readily transportable, or smaller but still inflexible in use. Attempts to develop more versatile, small transportable systems have been made, but to date no known system meets all the requirements to overcome the problems of the prior art.

SUMMARY OF THE INVENTION

According to the present invention there is provided light measurement apparatus comprising an elongate member, said elongate member having at one end thereof light-emitting means and light-detecting means, at least the end of said elongate member provided with said light-emitting means and said light-detecting means being surrounded by a resiliently biassed sheath whereby in use when said elongate member is applied to a surface to take a reading said sheath defines a light-tight enclosure.

Preferably, the light-emitting and light-detecting means may comprise electronic components such as photodiodes, phototransistors or the like whereby the dimensions at the end of the member (i.e. the "tip") may be small so that the apparatus may be applied to a small surface area. The provision of a sheath to define a light-tight enclosure enables a low intensity light source to be used as the light-emitting means, e.g. a light-emitting diode (LED).

The light-emitting means may comprise means for emitting broad spectrum light or light of limited wavelength ranges. The use of two or more narrow band emitters will allow simple spectral analysis to be performed. Such a possibility is particularly advantageous when it is desired to measure concentration ratio(s) of two or more components on the test site which absorb light of different wavelength bands/regions. In this latter arrangement, two or more separate light sources may be provided, e.g. two or more LEDs, or alternatively switchable filter means may be provided to a single light source. Since absorption spectra from coloured surfaces always are of a broad-band nature, the signal-to-noise (S/N) ratio can be improved during measurements by using broad-band light emitters which coincide with the absorption range.

The sheath is preferably adapted to be slidable between the position in which it defines a light-tight enclosure, and a position in which the end of the elongate member is exposed. This facilitates initial application of the apparatus to a small area, after which the sheath may be moved to define the light-tight enclosure. Preferably, indeed, the sheath may be biased, e.g. by resilient means such as a spring, into a position to expose the end of the elongate member. The end of the sheath adjacent the end of the elongate member may be provided with a sealing ring to further ensure a light-tight seal.

The operation of the apparatus to effect a measurement may simply be left for an operator's command. Preferably, however, the tip of the elongate member is provided with a light sensor (e.g. a phototransistor or the like) to be located within the light-tight enclosure. The light-sensor can be arranged to detect when it is sufficiently dark within the enclosure for a reliable accurate reading to be taken and via control circuitry may then cause a measurement to be taken.

In addition to defining a light-tight enclosure, the provision of a sheath member also has the advantage of helping to ensure that the apparatus is operated in the correct orientation, i.e. perpendicular to the surface to be measured.

It is also particularly preferred that the light-emitting means and the light-detecting means are arranged asymmetrically with respect to each other, to avoid any problems with light being directly reflected off a glossy surface. Indeed viewed from another aspect the invention provides light measurement apparatus comprising an elongate member having at one end thereof light-emitting means and light-detecting means, said light-emitting means and said light-detecting means being asymmetrically arranged with respect to the central axis of said elongate member.

BRIEF DESCRIPTION OF THE DRAWINGS

An embodiment of the invention will now be described by way of example and with reference to the accompanying drawings, in which.

DESCRIPTION

Figure 1:
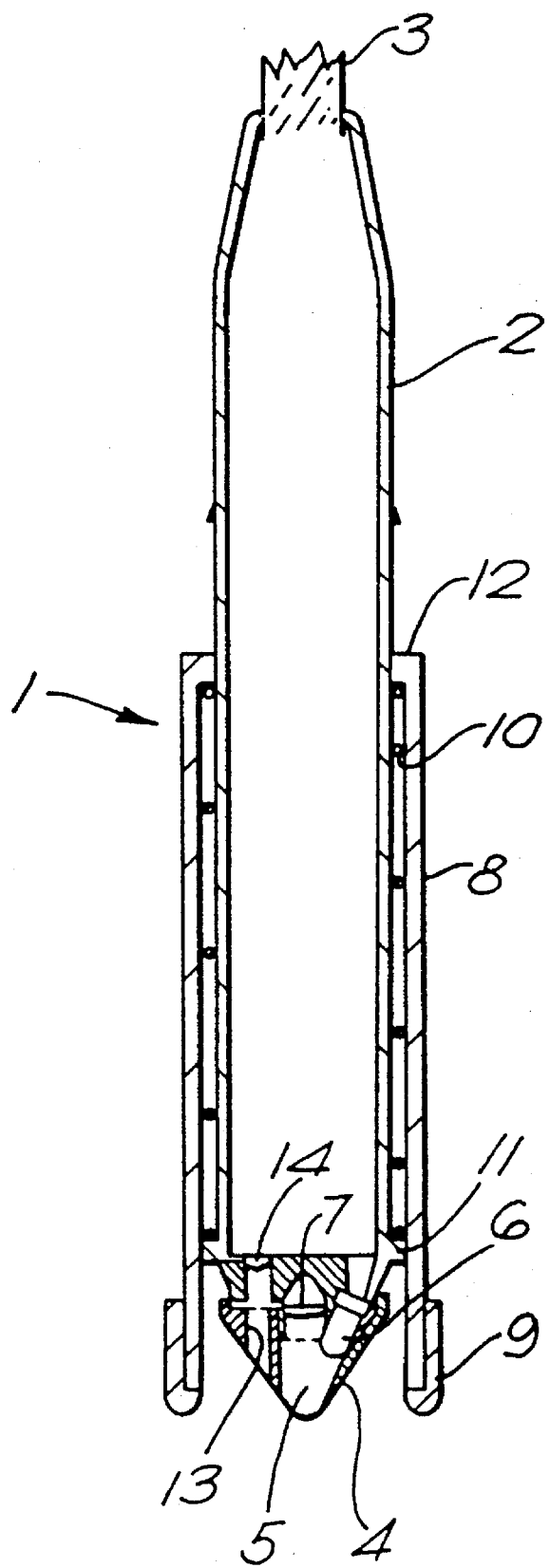
FIG. 1 is a sectional side view of apparatus according to an embodiment of the invention.

Referring first to FIG. 1 there is shown therein an elongate pen-like member 1 comprising a cylindrical housing 2. One end of the housing 2 is provided with an aperture for receiving a cable 3 by means of which the light-emitting, -detecting and -sensing elements (to be described below) may be operatively connected to a remote control unit such as a microprocessor (not shown). The apparatus may include light intensity measurement circuitry of the type disclosed in our co-pending application entitled "Light Measurement", the contents of which are incorporated herein by reference. The application referred to in the preceding sentence is International Patent Application No. PCT/GB93/01356 which has an international filing date of Jun. 29, 1993, which published as WO94/00742 on Jan. 6, 1994, and which is now lapsed because the national phase was not entered in any country.

The other end of the cylindrical housing 2 is closed by a base member and a conical tip member 4. The conical tip member 4 is formed with a hollow central chamber 5 within which are located light-emitting means in the form of a light-emitting-diode (LED) 6, and light-detecting means in the form of a photodiode 7. The chamber 5 opens to the exterior of the tip member 4 at the apex thereof which defines a measurement location which is positioned on the central longitudinal axis of the housing 2. Locating the LED 6 and photodiode 7 recessed within the conical tip member 4 both helps protect them from accidental damage and shields them partly from stray light.

Surrounding the lower half of the housing 2 is a cylindrical sheath 8 of light impermeable material, around the lower end of which is provided an annular sealing ring 9 formed for example of a resilient elastomeric material. A spring 10 is located between an annular shoulder 11 formed at a lower end of the housing 2 and an inwardly directed annular rim 12 formed at the upper end of sheath 8. The spring 10 normally biases the sheath 8 upwardly out of the position of FIG. 1 to expose the conical tip member 4. In use, the tip member 4 is applied to the surface to be measured and subsequently the sheath 8 is moved downwardly against the spring bias until the sealing ring 9 contacts the surface around the region to be measured. There is thus defined a light-tight enclosure within which are received the surface to be measured, and the light-emitting and detecting means.

A bore 13 is formed in the conical member 4 and the base of the housing 2 at the end of which remote from the exterior is provided a photo-transistor 14. The phototransistor 14 is adapted to sense when the light within the light-tight enclosure is below a minimum level for an accurate measurement to be taken. The phototransistor 14 then sends a signal to the control means to cause the LED 6 to operate to take a measurement.

Figure 2:
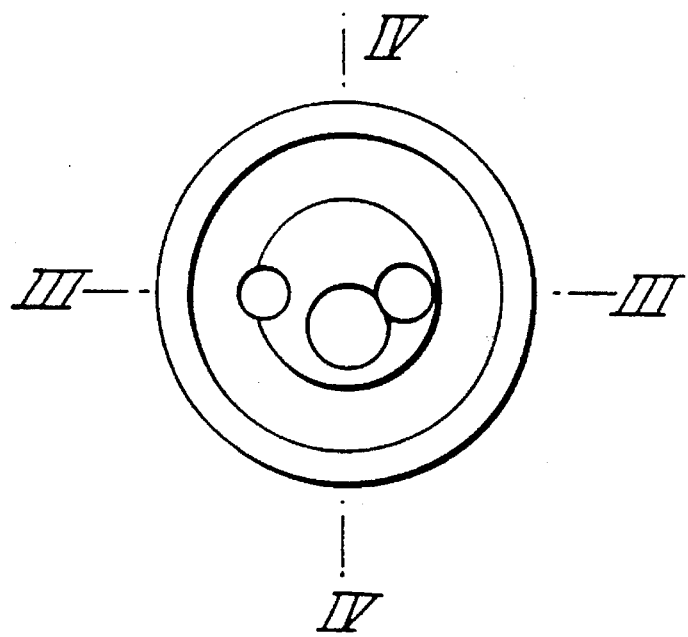
FIG. 2 is a cross-section through the apparatus in the region of the tip thereof.
Figure 3:
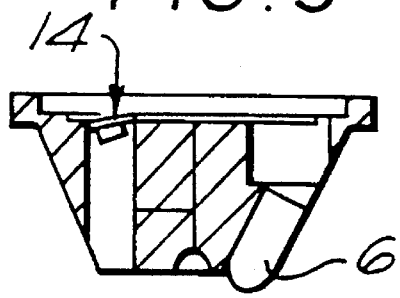
FIG. 3 is a view along line III—III.
Figure 4:
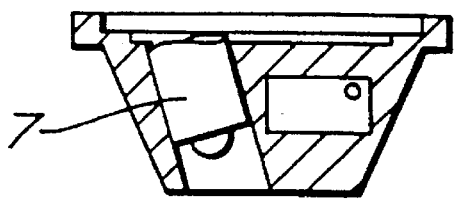
FIG. 4 is a view along line IV—IV.

As can be seen from FIGS. 2, 3 and 4, the LED 6 and photodiode 7 are positioned asymmetrically with respect to each other and the central longitudinal axis of the housing whereby if the apparatus is applied to a glossy surface, directly reflected light from the LED 6 cannot be received by the photodiode 7.

Although the invention has been described with particular reference to colour measurement, it will be appreciated that the range of applications is wider and, for example, with suitable programming of the control means, the invention could be applied to a bar-code reader, e.g. for up-dating the apparatus with new test data.

It should also be understood that although reference is made in this specification to the term "light", it is not intended that the invention be limited to visible light, but rather the invention may also extend to the non-visible parts of the electromagnetic spectrum.

In addition to solid phase immunoassay test cards, the apparatus may of course also be used to measure relative colour intensity in other analytical methods giving rise to coloured responses, e.g. dot/spot immunoassays and electrophoretic blotting systems.

What is claimed is:

1. Light measurement apparatus comprising an elongate member (1), said elongate member having at one end thereof light-emitting means (6) and light-detecting means (7), at least the end of said elongate member with said light-emitting means (6) and said light-detecting means (7) being surrounded by a resiliently biased sheath (8) whereby in use when said elongate member (1) is applied to a surface to take a reading said sheath (8) is in a position in which it defines a light-tight enclosure.

2. Apparatus as claimed in claim 1 in which the light-detecting means is a photodiode.

3. Apparatus as claimed in claim 1 or claim 2 in which the light-emitting means is a light-emitting diode.

4. Apparatus as claimed in claim 1, in which at least two light-emitting means are provided to emit light at different wavelengths.

5. Apparatus as claimed in claim 1, in which the resiliently biased sheath is slidable between the position in which it defines the light-tight enclosure, and a position in which the end of the elongate member is exposed.

6. Apparatus as claimed in claim 5 in which an end of the sheath adjacent the end of the elongate member is provided with a sealing ring.

7. Apparatus as claimed in claim 1, in which the elongate member is in a perpendicular orientation relative to said surface when in the sheath defines the light-tight enclosure.

8. Apparatus as claimed in claim 1, in which a tip of the elongate member is provided with a light sensor within the light-tight enclosure and control means whereby light measurement is only taken by the light-detecting means when it is sufficiently dark within the light-tight enclosure for a reliable accurate reading to be taken.

9. Apparatus as claimed in claim 1, in which the light-emitting means and light-detecting means are arranged asymmetrically with respect to a central axis of the elongate member.

10. A method of determining at least one of intensity and color of a colored spot on a surface of a test site by using apparatus comprising an elongate member which has at one end thereof light-emitting means and light-detecting means wherein the end with the light-emitting means and the light-detecting means is surrounded by a resiliently biased sheath, the method comprising:

bringing the end of the elongate member with the light-emitting means and light-detecting means into contact with the surface;

pressing the resiliently biased sheath towards the surface to define a light-tight enclosure; and measuring at least one of the intensity and color of the colored spot on the surface.

11. The method of claim 10 wherein the colored spot is about 5 millimeters in size.

12. The method of claim 10 wherein the colored spot is derived from a solid phase immunoassay.

13. The method of claim 10 wherein the colored spot is derived from a dot/spot immunoassay.

14. The method of claim 10 wherein the colored spot is derived from an electrophoretic blotting system.

* * * * *